(12) United States Patent
Ito

(10) Patent No.: US 7,232,579 B2
(45) Date of Patent: Jun. 19, 2007

(54) COMPOSITION CONTAINING A MARINE-DERIVED INORGANIC SUBSTANCE AND CHITIN/CHITOSAN, AND METHOD OF PRODUCING THE COMPOSITION

(75) Inventor: Michio Ito, Nagano (JP)

(73) Assignee: Matsumoto Dental University, Nagano (JP)

( * ) Notice: Subject to any disclaimer, the term of this patent is extended or adjusted under 35 U.S.C. 154(b) by 503 days.

(21) Appl. No.: 10/940,998

(22) Filed: Sep. 15, 2004

(65) Prior Publication Data

US 2005/0058715 A1    Mar. 17, 2005

(30) Foreign Application Priority Data

Sep. 17, 2003   (JP) .............................. 2003-324229

(51) Int. Cl.
- A61K 6/06 (2006.01)
- A61K 31/722 (2006.01)
- A61K 33/08 (2006.01)
- A61K 33/30 (2006.01)
- A61K 33/42 (2006.01)
- A61K 35/12 (2006.01)
- A61K 35/36 (2006.01)
- A61K 35/60 (2006.01)

(52) U.S. Cl. ........................ 424/574; 424/520; 424/522; 424/543; 424/572; 424/601; 424/641; 424/642; 424/643; 424/688; 424/724; 514/55; 514/769; 514/772

(58) Field of Classification Search ................ 424/520, 424/522, 543, 572, 574, 601, 641, 642, 643, 424/688, 724; 514/55, 769, 772
See application file for complete search history.

(56) References Cited

U.S. PATENT DOCUMENTS

| | | | |
|---|---|---|---|
| 5,420,248 | A | 5/1995 | Devictor et al. |
| 5,880,109 | A | 3/1999 | Nakamura et al. |
| 6,214,048 | B1 | 4/2001 | Ito et al. |
| 6,271,350 | B1 | 8/2001 | Shimizu et al. |

FOREIGN PATENT DOCUMENTS

| | | |
|---|---|---|
| EP | 1 053 739 A1 | 11/2000 |
| JP | 5-220211 | 8/1993 |
| JP | 7-194316 | 8/1995 |
| JP | 2722014 | 11/1997 |
| JP | 2000-50811 A | 2/2000 |
| JP | 2001-200000 A | 7/2001 |

OTHER PUBLICATIONS

Biosis abstract, accession No. 2000:97123 (Mar. 2000).*
Malafaya et al., "Porous Bioactive Composites from Marine Origin Based in Chitosan and Hydroxylapatite Particles," Key Engineering Materials, vols. 240-242, 2003, pp. 39-42.
Hiroyuki et al, "Separationo f hydroxyapatite from scales of fish," Database Compendex Online, XP002308478, Engineering Information, Inc., 1996.

* cited by examiner

*Primary Examiner*—John Pak
(74) *Attorney, Agent, or Firm*—Foley & Lardner LLP

(57) ABSTRACT

A composition contains an inorganic substance obtained as a residue after incinerating skins of marine organisms, and chitin/chitosan. The composition is obtained by incinerating the skins of the marine organisms at a temperature within a range between 600° C. and 1000° C. to obtain the inorganic substance as a residue, obtaining a powdered inorganic substance from the inorganic substance, and kneading the powdered inorganic substance with chitin/chitosan powder.

9 Claims, 2 Drawing Sheets

COMPOSITION CONTAINING A MARINE-DERIVED INORGANIC SUBSTANCE AND CHITIN/CHITOSAN, AND METHOD OF PRODUCING THE COMPOSITION

This application claims priority to prior Japanese patent application JP 2003-324229, the disclosure of which is incorporated herein by reference.

BACKGROUND OF THE INVENTION

This invention relates to a composition containing an inorganic substance derived from skins of marine organisms and chitin/chitosan, and to a method of producing the composition.

In the medical field, a composition as a medical biomaterial is known. As a specific example, a composition for jaw bone regeneration is known in the field of dental treatment. The composition is called an osteoconduction substance.

When the osteoconduction substance is implanted or embedded between a jaw bone and gingiva after a surgical treatment for a periodontal disease, the osteoconduction substance exhibits an ability of creating a new bone by a function of increasing osteoblasts. Alternatively, the osteoconduction substance creates a new bone if it is implanted in the vicinity of a bone or into a bone.

The osteoconduction substance is produced by preparing a powder mixture of apatite and animal bone meal and kneading the powder mixture with chitosan sol obtained by dissolving chitosan by an acidic aqueous solution. In most cases, the animal bone meal is obtained from bone tissues of domestic animals, such as bovine bones and pig bones (for example, see Japanese Patent Application Publication (JP-A) No. H5-220211).

Recently, however, a problem of BSE (bovine spongiform encephalopathy) is exposed. In particular, it is pointed out that the osteoconduction substance using bovine bone powder as a material brings a potential risk of human infection by a pathogenic agent. Thus, in the medical field, it is desired to obtain a novel composition in view of the safety and a limited amount of resources.

SUMMARY OF THE INVENTION

It is an object of this invention to provide a composition which is capable of promoting bone formation and which is excellent in safety.

It is another object of this invention to provide a composition which is excellent in economical efficiency in view of waste recycling.

According to this invention, there is provided a composition containing an inorganic substance obtained as a residue after incinerating skins of marine organisms, and chitin/chitosan.

According to this invention, there is also provided a method of producing a composition, the method comprising the steps of incinerating skins of marine organisms at a temperature within a range between 600° C. and 1000° C. to obtain an inorganic substance as a residue, obtaining a powdered inorganic substance from the inorganic substance, and kneading the powdered inorganic substance with chitin/chitosan powder.

DESCRIPTION OF THE PREFERRED EMBODIMENTS

A composition according to this invention contains an inorganic substance obtained as a residue after incinerating skins of marine organisms, and chitin/chitosan.

In this embodiment, use is made of two kinds of inorganic substances as samples SAB and SAA.

Sample SAB

The inorganic substance as the sample SAB was obtained as a residue after incinerating skins of marine organisms. The amount of the inorganic substance extracted after incineration was about 65 wt % with respect to the weight of the skins of the marine organisms before incineration as 100%. In this embodiment, skins of salmon were used as the skins of the marine organisms.

The inorganic substance as the sample SAB comprises 54.8% $P_2O_5$ (phosphorus oxide), 35.4% CaO (calcium oxide), 5.0% MgO (magnesium oxide), 4.1% $SiO_2$ (silicon dioxide), 0.3% $K_2O$ (potassium oxide), 0.2% ZnO (zinc oxide), and 0.2% Fe (iron).

The inorganic substance as the sample SAB was visually observed by the use of a photograph taken by an electron microscope. As a result, presence of a number of voids randomly adjacent to one another was confirmed. An average surface area of the voids was 5 to 300 μm.

Sample SAA

The inorganic substance as the sample SAA was obtained by immersing the skins of the marine organisms into hot water to extract collagen and thereafter incinerating the skin to leave the inorganic substance as a residue. The amount of the inorganic substance extracted after incineration was about 55 wt % with respect to the weight of the skins of the marine organisms before incineration as 100%. As the skins of the marine organisms, skins of salmon were used.

The inorganic substance as the sample SAA comprises 58.8% $P_2O_5$, 32.8% CaO, 4.7% MgO, 3.5% $SiO_2$, 0.1% ZnO, and 0.1% other substances.

The inorganic substance as the sample SAA was visually observed by the use of a photograph taken by the electron microscope. As a result, presence of a number of voids randomly adjacent to one another was confirmed. An average surface area of the voids was 5 to 300 μm.

In order to extract collagen from the skins of the marine organisms, use may be made of various well-known techniques. For example, a method of extracting collagen from skins of fishes is disclosed in Japanese patent (JP-B) No. 2722014 and Japanese Patent Application Publication (JP-A) Nos. 2000-50811 and 2001-200000.

As the skins of the marine organisms, use may be made of skins of trout, walleye pollack (Alaska pollack) or cod, shark or dogfish, Atka mackerel, halibut, or tuna. It is noted here that the marine organisms used for obtaining the inorganic substance are not restricted to those mentioned above. It is desired to select the skins of the marine organisms for obtaining the inorganic substance taking a limited amount of resources and productivity into consideration.

Figure 1:
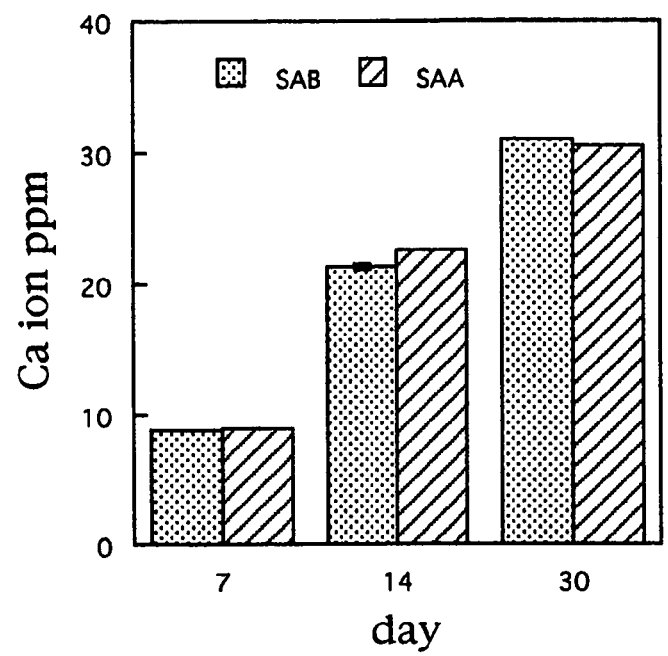
FIG. 1 is a graph showing the amounts of release of Ca ions in inorganic substances used in a specific embodiment of this invention.
Figure 2:
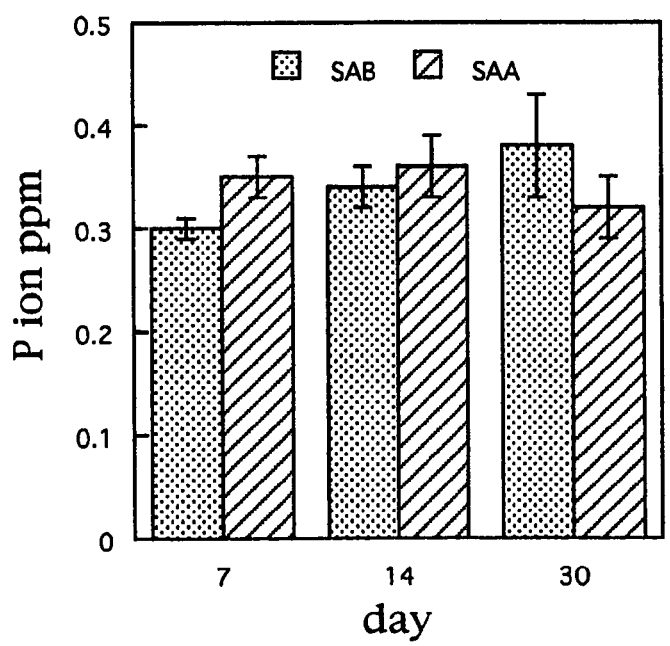
FIG. 2 is a graph showing the amounts of release of P ions in the inorganic substances used in the specific embodiment of this invention.
Figure 3:
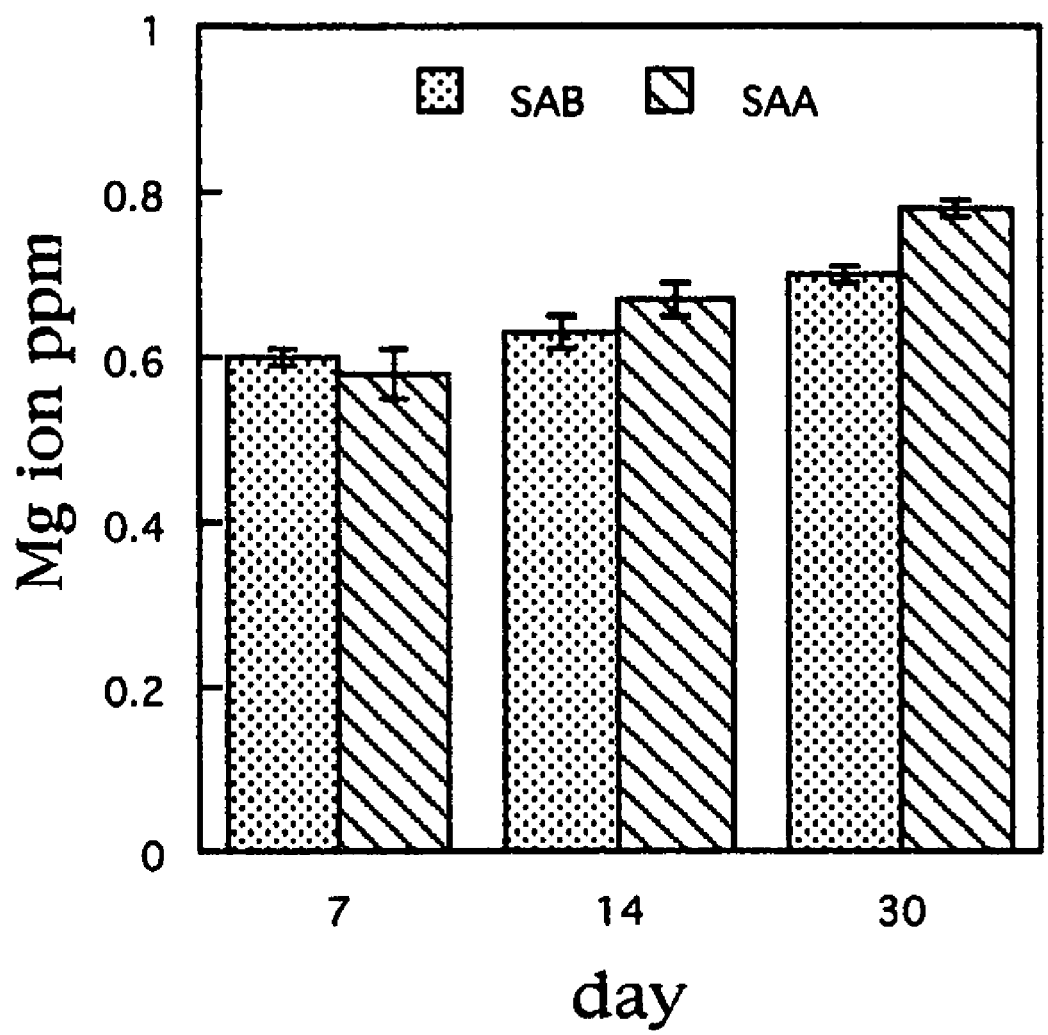
FIG. 3 is a graph showing the amounts of release of Mg ions in the inorganic substances used in the specific embodiment of this invention.

Referring to FIGS. 1, 2, and 3, the inorganic substances as the samples SAB and SAA were bathed or immersed in a physiological salt solution. After 7 days, 14 days, and 30 days, the amount of release (ppm) of each of Ca ions, P ions, and Mg ions was measured.

As is obvious from FIGS. 1 through 3, in the inorganic substance as the sample SAB, the amount of release of each of Ca ions, P ions, and Mg ions was increased with lapse of time.

In the inorganic substance as the sample SAA, the amount of release of each of Ca ions and Mg ions was increased with lapse of time. However, the amount of release of P ions was slightly decreased after 30 days.

As described above, in the inorganic substances as the samples SAA and SAB, the amounts of release of those ions were generally increased with lapse of time. Thus, it has been confirmed that those ions are released and absorbed in a living body.

The inorganic substance mentioned above is kneaded with chitin/chitosan to produce a composition suitably used in various applications, such as a medical biomaterial.

Hereinafter, description will be made of a method of producing the composition containing the inorganic substance and chitin/chitosan.

The inorganic substance as the sample SAB is obtained in the following manner. The skins of the marine organisms are incinerated at a temperature within a range between 600° C. and 1000° C. to leave, as a residue, the inorganic substance as the sample SAB.

On the other hand, the inorganic substance as the sample SAA is obtained in the following manner. The skins of the marine organisms are immersed in hot water to extract collagen from the skins. After extraction of collagen, the skins are incinerated at a temperature within a range between 600° C. and 1000° C. to leave, as a residue, the inorganic substance as the sample SAA.

Then, the inorganic substance SAB or SAA is kneaded with chitin/chitosan sol obtained by dissolving chitosan powder by an acidic aqueous solution. For the acidic aqueous solution, use may be made of one of acetic acid, lactic acid, malic acid, citric acid, adipic acid, tartaric acid, malonic acid, and the like. By kneading the inorganic substance and the chitin/chitosan sol a sol material is obtained.

Thereafter, the sol material is neutralized with an aqueous solution containing a compound. The sol material is hardened in the aqueous solution in 3 to 60 minutes to obtain a composition having a pH within a range of 7.0 to 10.0. For example, the compound used to neutralize the sol material is calcium oxide.

Then, the composition is dehydrated. After dehydration, the composition has a brittle or fragile nature, like biscuits. The composition may be used as an osteoconduction substance as a medical material.

Before the osteoconduction substance is implanted into a living body as a biomaterial, an aqueous solution (which will later be described) is absorbed into the osteoconduction substance to produce a gel film having elasticity like rubber and a predetermined strength. Thereafter, the osteoconduction substance as the gel film is cut into a predetermined shape in conformity with the size of a diseased part of the living body and implanted into a treated site of the diseased part of the living body. For example, after a surgical operation for a periodontal disease, the osteoconduction substance is inserted between a jaw bone and gingiva to regenerate a new jaw bone.

When the osteoconduction substance is used in bone regeneration, new blood vessels are grown and spread into small voids in the organic substance and the inorganic substance is surrounded by cells. Around the inorganic substance, osteoblast activity is exhibited and osteoconduction is quickly attained.

Chitin/chitosan serves to fix a powdered inorganic substance to a diseased part of a living body. At the time when chitin/chitosan is absorbed into the living body, an osteoid tissue is observed and transformed into a bone.

Upon production of the gel film, the aqueous solution is absorbed into the osteoconduction substance. As the aqueous solution, use may be made of a physiological salt solution, an aqueous solution of sodium chloride, sodium bicarbonate, or sodium polyphosphate, a Ringer solution, or the like.

As described above in connection with the specific embodiment, the composition has a number of small voids formed in the organic substance. When the composition is used as the osteoconduction substance, the new blood vessels are readily spread into the small voids in the inorganic substance. Around the inorganic substance, the osteoblast activity is exhibited to promote osteoconduction.

In order to produce the composition, it is possible to use the skins of the marine organisms to be disposed of as waste after bodies of the marine organisms are used or after the skins themselves are used to extract collagen. In this case, economic efficiency is excellent in view of waste management and recycling.

Further, the inorganic substance is a natural mineral having a number of small voids formed inside. Therefore, the composition containing the inorganic substance may be used in various applications, such as a food additive material for use as a food additive for remineralizing, a supplementing agent contained in a tablet or a capsule, a filtering material for deprotenization, various kinds of medical biomaterials, various kinds of cosmetic materials, and so on.

While this invention has thus far been described in connection with the preferred embodiment thereof, it will readily be possible for those skilled in the art to put this invention into practice in various other manners without departing from the scope set forth in the appended claims.

What is claimed is:

1. A composition containing an inorganic substance obtained as a residue after incinerating skins of marine organisms at a temperature within a range between 600° C. and 1000° C., and a mixture of chitin and chitosan.

2. The composition according to claim 1, wherein said inorganic substance is a residue after extracting collagen from said skins.

3. The composition according to claim 1, wherein each of said inorganic substance and chitin/chitosan is in a powder state.

4. The composition according to claim 1, wherein said inorganic substance at least contains $P_2O_5$, $CaO$, $MgO$, $SiO_2$, and $ZnO$.

5. The composition according to claim 1, wherein said composition is present in an amount sufficient to be used as a supplementing agent for a tablet or capsule, a deproteinizing filtering material, a dental material, a medical biomaterial, a food additive material, or a cosmetic material.

6. A method of producing a composition, said method comprising the steps of:
   incinerating skins of marine organisms at a temperature within a range between 600° C. and 1000° C. to obtain an inorganic substance as a residue;
   obtaining a powdered inorganic substance from said inorganic substance; and
   kneading the powdered inorganic substance with a powder mixture of chitin and chitosan.

7. The method according to claim 6, wherein said inorganic substance is obtained by incinerating the skins after collagen is extracted from the skins.

8. The method according to claim 6, wherein said inorganic substance at least contains $P_2O_5$, $CaO$, $MgO$, $SiO_2$, and $ZnO$.

9. The method according to claim 6, wherein said composition is present in an amount sufficient to be used as a supplementing agent for a tablet or capsule, a deproteinizing filtering material, a dental material, a medical biomaterial, a food additive material, or a cosmetic material.

* * * * *